United States Patent
Sievers

(10) Patent No.: US 7,325,553 B2
(45) Date of Patent: Feb. 5, 2008

(54) METHOD OF FLOSSING AND FLOSSING AID SYSTEM

(75) Inventor: Mark William Sievers, 9317 Thomas Ave. North, Brooklyn Park, MN (US) 55444

(73) Assignee: Mark William Sievers, Brooklyn Park, MN (US)

( * ) Notice: Subject to any disclaimer, the term of this patent is extended or adjusted under 35 U.S.C. 154(b) by 0 days.

(21) Appl. No.: 10/985,728

(22) Filed: Nov. 9, 2004

(65) Prior Publication Data

US 2005/0109366 A1    May 26, 2005

Related U.S. Application Data

(60) Provisional application No. 60/518,979, filed on Nov. 10, 2003.

(51) Int. Cl.
*A61C 15/00* (2006.01)
(52) U.S. Cl. .................................... 132/323
(58) Field of Classification Search ............... 132/321, 132/323, 324, 325, 309; 248/304, 305.5; 2/16, 20, 21; 206/581, 368, 63.5; 63/15.45, 63/15.5, 15.6, 15.65
See application file for complete search history.

(56) References Cited

U.S. PATENT DOCUMENTS

| 805,664 | A | 11/1905 | Ramage |
| 1,235,605 | A | 8/1917 | Sauer |
| 2,389,237 | A | 11/1945 | Petrullo |
| 3,214,939 | A | * 11/1965 | Monahan ................ 63/15.6 |
| 3,696,821 | A | 10/1972 | Adams, IV |
| 3,802,445 | A | 4/1974 | Wesley |
| 3,831,611 | A | 8/1974 | Hendricks |

(Continued)

FOREIGN PATENT DOCUMENTS

GB    2 362 310    11/2001

(Continued)

OTHER PUBLICATIONS

Klutz—Gelly Bands®, http://www.klutz.com/catalog/product. php?itemNo=1430&cat=7, 2 pages, (TM and © 2005) commercially available prior to Nov. 10, 2002.

(Continued)

*Primary Examiner*—Todd E. Manahan
*Assistant Examiner*—Rachel A. Running
(74) *Attorney, Agent, or Firm*—Merchant & Gould, P.C.

(57) ABSTRACT

A method of flossing and flossing system utilize a piece including stretchable and flexible material having an inner and an outer surface. The piece is adapted to be placed around a finger on a hand. The method includes placing the piece around a finger of a first floss-receiving hand; providing a length of non-soiled dental floss; tightly winding a segment of the length of floss around the piece so that the segment of floss overlaps itself at least once; taking another segment of the length of floss with another floss-feeding hand so that a flossing segment of the length of floss is left between the two hands for flossing teeth; and flossing using the flossing segment of the length of floss between the two hands. Also a dental floss system includes the piece and a length of dental floss.

20 Claims, 10 Drawing Sheets

U.S. PATENT DOCUMENTS

| | | | |
|---|---|---|---|
| 3,901,251 A | 8/1975 | Johnston | |
| 4,016,892 A | 4/1977 | Chodorow | |
| 4,037,433 A | 7/1977 | Weber | |
| 4,043,145 A * | 8/1977 | Chervin | 63/15 |
| 4,050,470 A | 9/1977 | Miller | |
| 4,342,324 A | 8/1982 | Sanderson | |
| 4,638,824 A | 1/1987 | De La Hoz | |
| 4,763,940 A | 8/1988 | Held | |
| 4,790,336 A | 12/1988 | Kuo | |
| 4,903,507 A * | 2/1990 | Gesensway | 63/15.6 |
| D323,722 S | 2/1992 | Lott | |
| 5,222,510 A | 6/1993 | Zuehlsdorf | |
| 5,406,965 A | 4/1995 | Levine | |
| 5,435,330 A | 7/1995 | Dix | |
| 5,454,386 A | 10/1995 | Dix | |
| 5,477,871 A | 12/1995 | Sanchez, Jr. | |
| 5,503,168 A | 4/1996 | Wang | |
| 5,517,692 A * | 5/1996 | Wunderlich-Kehm | 2/21 |
| 5,653,246 A | 8/1997 | Wei et al. | |
| 5,680,875 A | 10/1997 | Winters | |
| 5,893,379 A | 4/1999 | Ghamaty-Azimi | |
| 6,065,480 A | 5/2000 | Mader | |
| 6,131,864 A * | 10/2000 | Schumann | 248/205.3 |
| 6,481,244 B1 * | 11/2002 | Wright | 63/15.8 |
| 6,526,991 B2 * | 3/2003 | Bodwalk | 132/309 |
| 6,557,853 B2 * | 5/2003 | Huettlinger | 273/148 B |
| 6,672,105 B1 * | 1/2004 | Sills | 63/15.6 |
| 2001/0039955 A1 | 11/2001 | Winters et al. | |

FOREIGN PATENT DOCUMENTS

| | | |
|---|---|---|
| GB | 2 370 489 | 7/2002 |
| JP | 60 114862 | 8/1985 |
| JP | 4 98172 | 8/1992 |

OTHER PUBLICATIONS 34792 unknown JP.

* cited by examiner

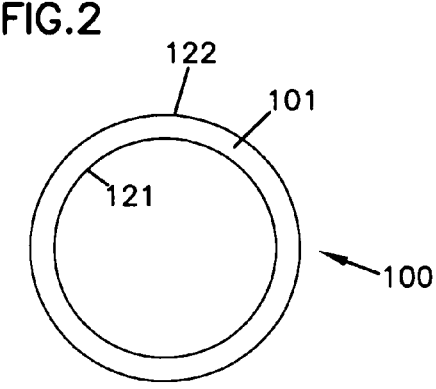
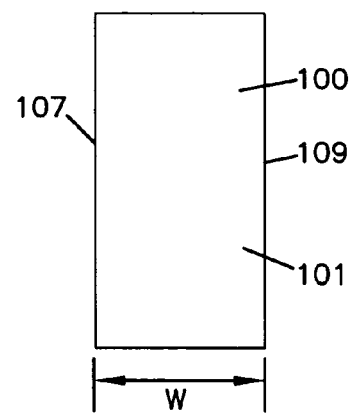
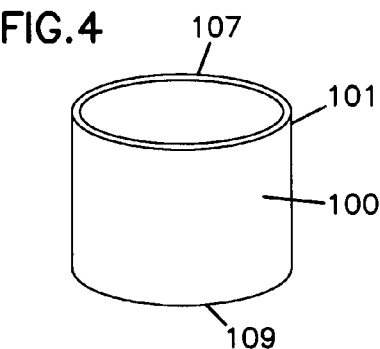
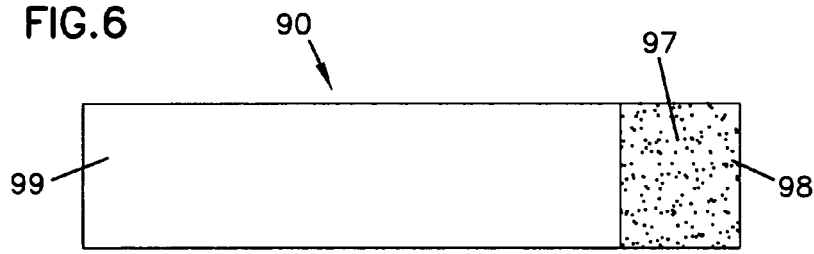
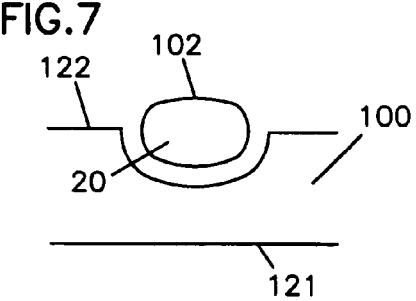

METHOD OF FLOSSING AND FLOSSING AID SYSTEM

This application is a utility patent application claiming priority to the provisional U.S. Patent Application Ser. No. 60/518,979 filed on Nov. 10, 2003, which application is incorporated herein by reference.

FIELD OF THE INVENTION

The present invention relates in general to a dental flossing system and method. More particularly, the invention provides a flossing system and method that facilitates dental flossing and reduces or eliminates finger discomfort associated with dental flossing.

BACKGROUND OF THE INVENTION

Flossing on a regular basis is a practice that has been highly recommended by dentists to reduce the amount of plaque built up around the gumline. The conventional method of flossing taught by dentists involves wrapping the free ends of a strand of dental floss around the middle fingers of each hand. The section of floss between the fingers is kept in tension to make it possible to penetrate the gaps between the teeth. For individuals with tight teeth, where the gaps between the teeth are quite narrow, a considerable amount of tension is needed for penetration of the gaps. Usually the index fingers, and sometimes the thumbs are used to guide the floss into and around the mouth and between each tooth. The floss is normally wrapped very tightly around the middle fingers of the hand to create the tension needed in the flossing section to penetrate the gaps between the teeth and to prevent the floss from slipping. In addition, as the floss gets used, fresh floss is normally fed from one hand to the other. The soiled floss, in turn, is wound onto the middle finger of the receiving hand. Anyone who has flossed knows that as the floss is wrapped around the finger of the receiving hand and tension is increased on the floss, flossing starts to become an uncomfortable experience. While one hand, which feeds new floss, gets discrete breaks from the pressure as new floss is fed, the finger on the receiving hand remains tightly wrapped the entire time. Each additional wrapping of the floss around the receiving finger creates more pressure build-up and cuts off the blood circulation in that finger. Further, the floss wrapped around the receiving finger is spent floss that is wet and soiled, causing additional discomfort to the user.

Dental floss devices/holders/applicators have been invented to attempt to reduce the pain and discomfort associated with flossing while trying to make it an easier experience. One such example is the design disclosed in U.S. Pat. No. 3,901,251. Generally, in most designs that have been introduced to attempt to reduce the pain and discomfort associated with flossing, the degree of success has been limited due to certain disadvantages. Many designs include a floss dispenser that is bulky and contain a sharp floss cutter that may cause discomfort when contacting the lips and the mouth. In designs that have used a ring-type floss receiver, the take-up rings often have a smooth outer surface that does not grip the floss securely. To secure the floss in place, either a thumb must hold the floss against the smooth surface of one of these ring-type floss receivers or the floss has to be wrapped several times around one of these floss receivers, resulting in wasted floss and wasted time. If a thumb is used to hold the floss to secure it, two fingers may end up entering the mouth to satisfactorily floss the teeth, which can be cumbersome. Also, in most ring-type designs, the rigidity or hardness of the components of the flossing aids have created discomfort when worn around the fingers, especially when the fingers are bent at the joints, or discomfort in the mouth.

Dental floss manufacturers have also attempted to reduce finger pain by making types of floss that is especially slippery to slide easily between the teeth to reduce some of the tension that gets built up. While this can reduce finger pain, such types of floss can be difficult to grip, which may be frustrating to a user.

Improved flossing aids, methods and flossing systems are needed in the art.

SUMMARY OF THE INVENTION

Generally, the present invention provides flossing aid systems utilizing an ergonomic, practical, reusable flossing aid that can be used in combination with any type of dental floss to eliminate pain caused by wrapping spent floss around a finger and methods of flossing using the flossing systems. In one particular embodiment of the invention, a method of flossing utilizes a piece of stretchable and flexible material having an inner and an outer surface, where the piece is adapted to be placed around a finger on a hand. The method includes placing the piece around a finger of a first floss-receiving hand; providing a length of non-soiled dental floss; tightly winding a segment of the length of floss around the piece so that the segment of floss overlaps itself at least once; grabbing another segment of the length of floss with another floss-feeding hand so that a flossing segment of the length of floss is left between the two hands for flossing teeth; and flossing using the flossing segment of the length of floss between the two hands.

In another embodiment of the invention, a dental floss system includes a length of dental floss and a piece of stretchable and flexible material having an inner and an outer surface wherein the piece is adapted to be placed around a finger on a hand.

BRIEF DESCRIPTION OF THE DRAWINGS

The invention may be more completely understood by considering the detailed description of various embodiments of the invention, which follows in connection with the accompanying drawings.

FIG. 2 is a top view of one embodiment of a flossing aid adapted for use with the dental floss system of FIG. 1;

FIG. 3 is a side view of the flossing aid of FIG. 2;

FIG. 4 is a perspective view of the flossing aid of FIG. 2;

FIG. 6 is a top view of an alternative embodiment of a flossing aid adapted for use with the dental floss system of FIG. 1;

FIG. 7 is a partial cross sectional view of the dental floss system of FIG. 1, taken along line 7-7 of FIG. 5A;

Figure 1:
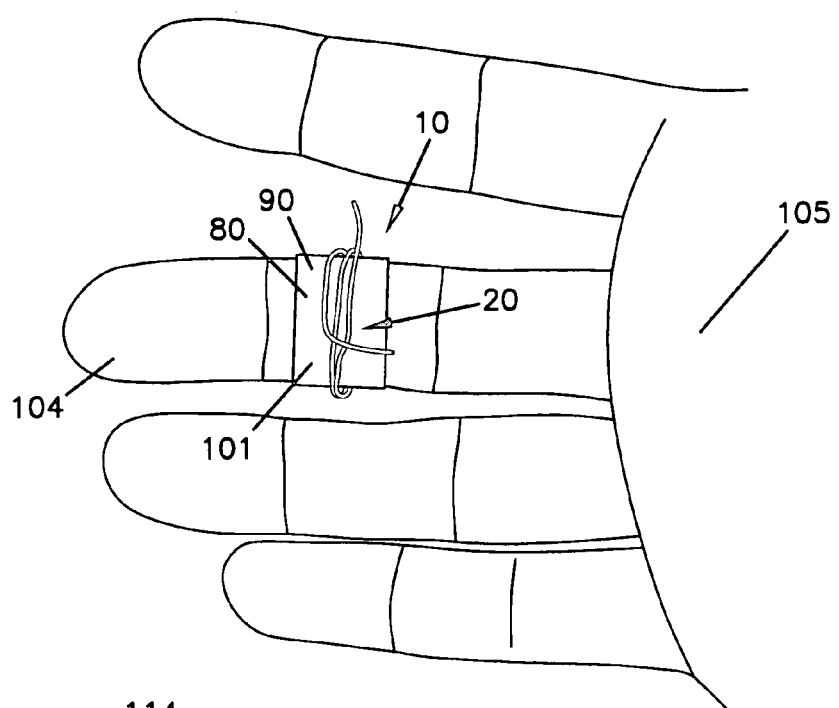
FIG. 1 is a side view of one embodiment of a dental floss system according to the invention, the dental floss system is shown placed around the middle finger of a hand.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENT

The present invention is believed to be applicable in the area of oral hygiene. The invention has been found to be particularly advantageous in application environments involving dental flossing.

While the present invention is not so limited, an appreciation of various aspects of the invention is best gained through a discussion of various application examples operating in such an environment.

Referring to FIG. 1, a dental floss system 10 according to the invention is illustrated. The dental floss system 10 includes a flossing aid 80 adapted to be placed around a finger 104 on a hand 106 and a length of dental floss 20 adapted to be wrapped around the flossing aid 80.

A. Flossing Aid

In FIG. 1, one particular embodiment of a flossing aid 80 including a piece 90 of stretchable and flexible material 101 is illustrated. It shall be understood that the piece 90 of stretchable and flexible material is only one example of many different kinds of flossing aids that can be used within the spirit of the invention. There are many other embodiments possible for the flossing aid 80 as shall be more clear from the following description.

For example, the flossing aid 80 as described herein may also be a continuous ring that is slipped onto the finger or a piece of material that is wrapped around a finger. The flossing aid 80 may also be a split ring rather than a continuous ring as will be described in further detail below. A continuous ring or a split ring are embodiments that are probably easier for a user to position on a finger for use in flossing than a piece of material that is wrapped around a finger.

For convenience, the flossing aid 80 of the invention will be described in terms of a ring throughout the disclosure except where stated, it being understood that the inventive aspects of the disclosure apply equally to other embodiments of the flossing aid such as a piece or a split ring. For example, where a ring and a method of using a ring are described herein, this description also applies to a split ring or a piece of material that can be wrapped around a finger.

Referring to FIGS. 2-4, a ring 100 includes an inner surface 121 and an outer surface 122. The ring 100 includes a first edge 107 and an opposing second edge 109 separated by the flexible material 101 that extends between the edges. The material 101 has a width W. The ring 100 is generally circular and is adapted to be placed around the finger 104 of the hand 106 as illustrated in FIG. 1.

Figure 5B:
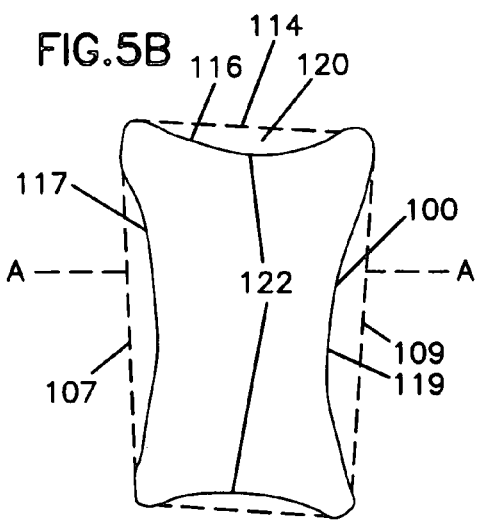
FIG. 5B is a side view of the flossing aid of FIG. 2, illustrating a deformed orientation of the flossing aid superimposed on an undeformed orientation of the flossing aid, the undeformed orientation is shown with phantom lines and the deformed orientation is shown with solid lines.
Figure 5A:
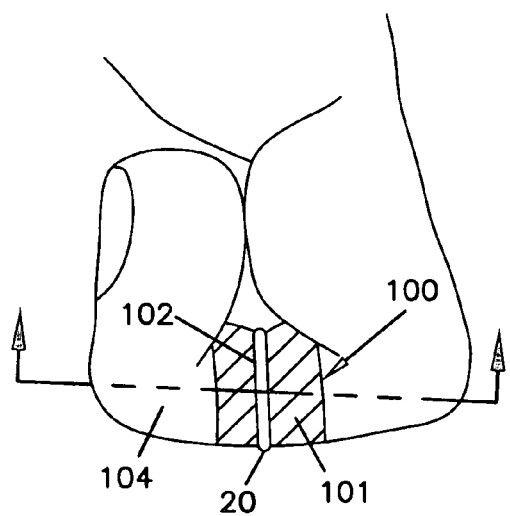
FIG. 5A is a perspective view of the dental floss system of FIG. 1, the finger to which the floss system is coupled is shown in a bent position.

As shown in FIG. 5A, after the ring 100 has been placed around the finger 104, as the finger 104 is bent, the ring 100 bends or deforms following the contour of the finger 104.

FIG. 5B illustrates the deformability characteristics of the ring 100 by illustrating a deformed ring superimposed on an undeformed ring. The ring 100 has an undeformed sideview perimeter 114 represented by the phantom lines and a deformed sideview perimeter 116 represented by a solid line. The ring 100 is adapted to be deformable in an axial direction along line A-A extending from the first edge 107 to the second edge 109. The first edge and/or the second edge 107 and 109, when deformed in an axial direction, are represented by reference numerals 117 and 119, respectively.

The ring 100 is also deformable in a direction perpendicular to the axial direction. The deformation of the cylindrical wall 120 of the ring 100 in the direction perpendicular to the axial direction is illustrated by the deformed portion 122.

The ring 100 according to the invention is sized to stretch and snugly fit around the finger 104 of the hand 106. Although FIG. 1 illustrates the ring 100 as being worn on the middle segment of the middle finger 104, the stretchability and the flexibility of the material 101 of the ring 100 makes it possible to place it around any segment of any finger of a hand. The ring returns to substantially its original shape after the force used to deform the ring is removed. It shall be understood that the ring is preferably made from materials that are elastically deformable. In other embodiments, the ring may be made from materials that tend to be slightly larger after stretching though the ring would return to close near its original size.

As discussed previously, instead of being a ring, a piece 90 of material may serve as a flossing aid, where the piece is shaped to be wrapped around a user's finger. Such a piece 90 is illustrated in FIG. 6 and will be briefly described. The piece 90 may include a rectangular shape as shown in FIG. 6. The rectangular piece 90 includes two ends 98 and 99. The rectangular piece may include an attachment mechanism 97 to connect the two ends 98 and 99 to form a continuous ring type design. The attachment mechanism may include any form of conventional attachment methods such as hook and loop fasteners, or, mating connectors utilizing male and female components such as grooves and channels or nubs and holes, or other attachment devices such as Velcro® or other types of adhesives. When attached, portions of the two ends 98 and 99 may overlap to varying extents depending on the attachment design used and the desired size.

The flossing aid may be made of many different types of material. For example, the ring 100 may be made of natural or synthetic rubber, synthetic polyisoprene, EPDM (Ethylene Propylene Diene Monomer) or silicone compounds. One specific example of a workable material is a synthetic formulation of polyisoprene known commercially as Natsyn® 2200 synthetic rubber. Such bands are available from many sources including Alliance Rubber Co., Hot Springs, Ark. The material is preferably latex-free to reduce allergic reactions in the skin since the system according to the invention is to be utilized in the context of dental flossing. The material is also preferably waterproof.

The flexible and stretchable portions of the ring material may have a thickness of about 0.028 inch to 0.045 inch, about 0.033 inch to 0.042 inch, about 0.033 inch to about 0.037 inch or about 0.035 inch. In one embodiment, the flexible and stretchable portions of the ring material may be 0.04 inch. In another embodiment, the ring is about 0.035 inch thick and is made of Natsyn® 2200 synthetic rubber. The thickness need not be uniform throughout the ring material and can vary according to desired functionality. For example, the ring may have portions with thicknesses that exceed these given dimensions.

In one embodiment, the flossing aid may be configured so that when placed around the finger, a tightly wound segment of a length of floss overlapping itself at least once when wound around the outer surface of the piece does not slip relative to the piece when the floss is pulled in tension. In one embodiment, when one end of a length of Johnson & Johnson Reach® Waxed floss is secured to a 1 lb weight, the weight being placed on the ground, the other end of the floss being wrapped around a finger wearing the flossing aid, the floss overlapping itself once, the crossing section of the floss being positioned on the finger so that the finger is between the crossed section of the floss and the ground, the flossing aid holds the floss securely in place without slipping for at least five seconds when the hand lifts the weight off the ground. The hand is placed with the palm side up and the finger wearing the flossing aid is slightly bent similar to the illustration shown in FIG. 5A when this test is performed. In another embodiment, the same results are achieved with a 2.5 lb weight. In yet another embodiment, the same results are achieved with the floss being wrapped around the finger wearing the flossing aid such that the floss overlaps itself twice. In yet another embodiment, the same results are achieved using Glide® Original floss. The durometer of the ring material impacts the ring's ability to hold the floss in this way. In certain embodiments, the durometer of the ring material may be about 20 to 65, about 25 to 55, about 28 to 45, or about 30. In certain other embodiments, the durometer of the ring material may be about 30 to 65, about 35 to 55, about 40 to 50, or about 44. The durometer of the ring need not be uniform throughout the ring material. Different combination of durometer values may be used on different portions of the ring according to different functionality needs.

The static coefficient of friction of the outer surface of the ring material may also impact the ring's ability to hold the floss as will be described in further detail below. In one embodiment, the outer surface of the ring material has a coefficient of friction like a Sterling™ rubber band by Alliance Rubber Co., which is made of a 0.035 inch thick piece of Natsyn® 2200 synthetic rubber.

The ring 100 according to the invention can come in different sizes, circumferences, lengths, widths, and/or material thicknesses. In one embodiment of the ring 100, the ring may come in 1 to 4 sizes, having a circumference range from approximately 1.75 to 2.5 inches, allowing it to comfortably fit children through large adults. A ring having a diameter sized to fit around more than one finger at the same time is also an embodiment contemplated within the scope of the invention. The width W, although it can change according to desired need, preferably should be at least ½ inch. The width W of the ring need not be uniform throughout the material, and may vary in dimension in different parts of the ring according to desired functionality.

As shown in FIG. 5A, the dental floss system 10 also includes a length of dental floss 20 used in combination with the flossing aid 80 (e.g., the ring 100) according to the invention. A length of dental floss 20 is wrapped around the ring 100 after the ring 100 has been placed on the finger 104. A segment 102 of the length of the dental floss 20 is then wrapped tightly around the outer surface 122 of the ring 100.

The floss 20 is wrapped to overlap itself at least once around the outer surface 122 of the ring 100. This wrapped segment 102 of the length of floss 20 stays secure on the outer surface 122 of the ring 100 when the floss is pulled in tension as discussed earlier. In certain embodiments, at least the outer surface 122 of the ring 100 is adapted to flex or deform as floss 20 is pressed into it. In one embodiment, the entire thickness of the material 101 flexes or deforms uniformly as the floss is pressed into it. In an alternative embodiment, the outer surface of the material deforms more than the inner surface. The flexibility of the material 101 helps grip the floss. The flexible and stretchable material 101 may include a coefficient of friction value so that the wrapped segment 102 does not slide as a tension force is applied on the length of floss 20. As the length of floss 20 is pulled with more force and the tension on the wrapped segment 102 is increased, the frictional force on the wrapped segment 102 increases. The frictional force is increased because a greater amount of force in the direction perpendicular to the outer surface 122 is applied on the ring, thus increasing the normal force applied to the wrapped floss 102 and thus the total amount of the frictional force.

FIG. 7 shows a cross-sectional view of a wrapped segment 102 of floss interacting with the material 101 of the ring 100. The floss 20 shown in FIG. 7 has an elliptical cross section. This cross sectional shape is for exemplary purposes only. Dental flosses with all other cross-sectional areas such as flat, circular, triangular, and others come within the scope of the invention and may be used with the flossing aid described herein. As the tension is increased on the wrapped segment 102 of the length of floss 20, the floss digs into the stretchable and flexible material 101 of the ring 100. As the floss 20 digs into the flexible material 101 of the ring 100, frictional force is applied around a substantial portion of the perimeter of the elliptical cross-section, not just on the bottom surface of the floss. In this manner, additional side friction is created on the wrapped segment 102 of the length of floss 20, securing the floss on the outer surface 122 of the ring 100 when the floss is pulled in tension. If the material 101 of the ring 100 flexes enough, the wrapped floss 102 may experience frictional forces even on the upper portion of the perimeter of its cross section, further increasing the total amount of frictional force applied to the floss. The same effect of increased friction may also be produced or increased whether or not the wrapped segment 102 of the length of floss 20 digs into the flexible material 101 of the ring 100.

It should also be understood that, even though the outer surface 122 of the ring may be desired to include a softer material with fair amount of friction to easily grasps floss, the inner surface 121 of the ring 100 may be provided with a material that is more slick that easily slides onto the finger. The slick interior surface may be provided around the entire inner perimeter or the ring or may be provided only at certain portions of the inner surface of the ring, as will be discussed further below. The slickness of the inner surface of the ring may be achieved by varying parameters such as the durometer, the hardness of the material, the coefficient of friction of the material, etc.

B. Storage and Packaging Options

Figure 17:
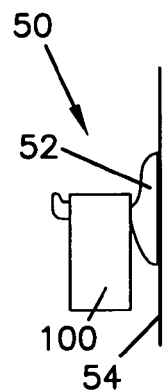
FIG. 17 is a side view of an embodiment of a hook device for storage of a flossing aid according to the invention.
Figure 18:
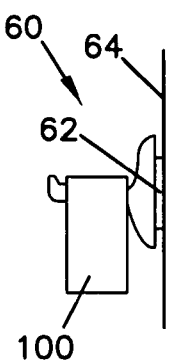
FIG. 18 is a side view of another embodiment of a hook device according to the invention.
Figure 19:
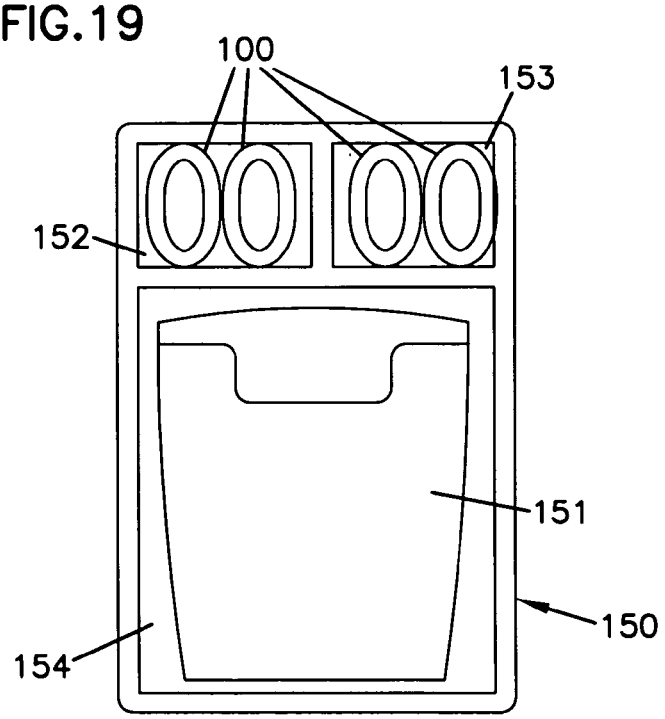
FIG. 19 is a top view of an embodiment of a container adapted to house a package of floss and a plurality of flossing aids according to the invention.
Figure 20:
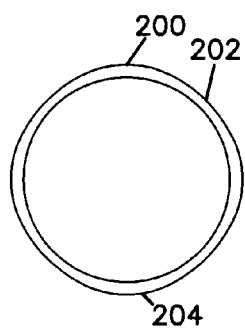
FIG. 20 is a top view of another alternative embodiment of a flossing aid adapted for use with the dental floss system of FIG. 1.
Figure 21:
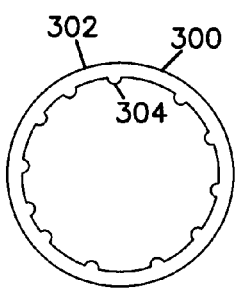
FIG. 21 is a top view of yet another alternative embodiment of a flossing aid adapted for use with the dental floss system of FIG. 1.
Figure 22:
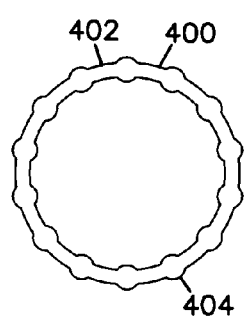
FIG. 22 is a top view of yet another alternative embodiment of a flossing aid adapted for use with the dental floss system of FIG. 1.
Figure 23:
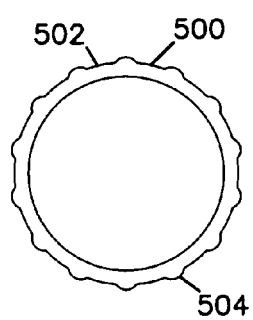
FIG. 23 is a top view of yet another alternative embodiment of a flossing aid adapted for use with the dental floss system of FIG. 1.
Figure 24:
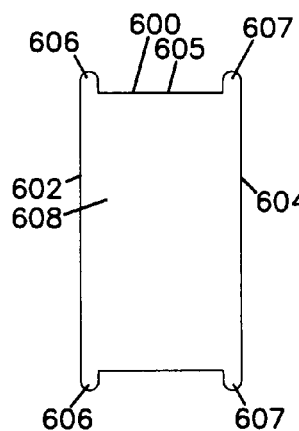
FIG. 24 is a side view of yet another alternative embodiment of a flossing aid adapted for use with the dental floss system of FIG. 1.

FIGS. 17-19 illustrate some examples of storage or packaging embodiments according to the invention. FIG. 17 illustrates a hook device 50 for storing one or more flossing rings 100 in a convenient manner. The hook device 50 includes a suction cup 52 for attachment to a smooth surface 54 by use of a vacuum seal. The hook device 60 illustrated in FIG. 18 uses a double-sided adhesive pad 62 that sticks to a vertical surface 64.

FIG. 19 illustrates an example of a container 150 used to house a package of floss 151 and one or more flossing rings 100. The container shown in FIG. 19 includes a separate compartment 154 for the floss package of floss 151 and separate compartments 152, 153 for the rings 100. A container 150 such as the one illustrated in FIG. 19 can have one or more lids. It may include one lid over the length of floss package 151, one or more lids over the ring 100 compartments, or just one lid over the entire case. The size and the shape of such a container illustrated in FIG. 19 can change according to desired functionality. The container 150 can be adapted to store different numbers of rings 100 or different shapes of floss packages.

C. Additional Flossing Aid Embodiments

FIGS. 20-23 illustrate top views of various embodiments of a flossing aid ring according to the invention. FIGS. 20-23 illustrate four different examples of rings 200, 300, 400, 500 wherein the rings include materials of varying thickness as discussed earlier. The material of varying thickness can include thinner sections 202, 302, 402, and 502 that stretch easily for comfort and thicker sections 204, 304, 404, and 504 that provide more padding for the finger to protect the finger from the pressure exerted by the floss.

FIGS. 24-27 illustrate side views of a number of embodiments of flossing aids providing some variations on the concept of having a varying material thickness. Ring 600 illustrated in FIG. 24 includes a first edge 602 and a second edge 604 and material 605 of varying thickness extending between the first edge 602 and the second edge 604. The material 605 includes flanges 606, 607 extending out radially from an outer surface 608 of the ring 600. The flanges 606, 607 are located at the first and second edges 602 and 604. The flanges 606, 607 are used as guides to assist the user in wrapping the floss on the ring 600.

Figure 25:
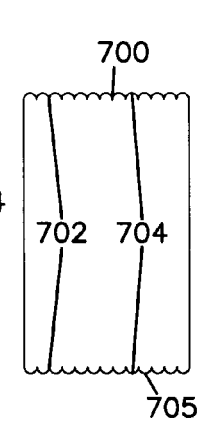
FIG. 25 is a side view of yet another alternative embodiment of a flossing aid adapted for use with the dental floss system of FIG. 1.

Ring 700 illustrated in FIG. 25 includes material 705 having a plurality of grooves 702 and bumps 704 defined by the material 701. These bumps 704 and grooves 702 are used to increase friction by creating larger contact surfaces to grip the cross sectional perimeter of the floss.

Figure 26:
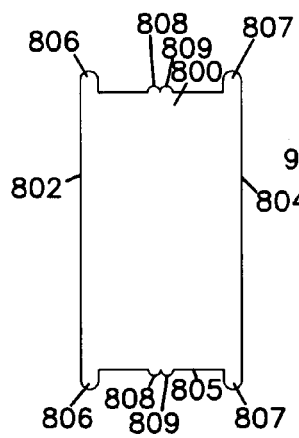
FIG. 26 is a side view of yet another alternative embodiment of a flossing aid adapted for use with the dental floss system of FIG. 1.

Ring 800 illustrated in FIG. 26 includes a first edge 802 and a second edge 804 and includes material 805 defining flanges 806, 807 extending out radially at the edges. Ring 800 also includes a couple flanges 808, 809 defined by the material at a location between the two edges 802 and 804. Flanges 808, 809 located in between the two edges 802 and 804 are useful for guiding the floss during wrapping and for anchoring and positioning the wrapped floss onto the ring in such a way that the floss overlaps itself every time it is wrapped.

Figure 27:
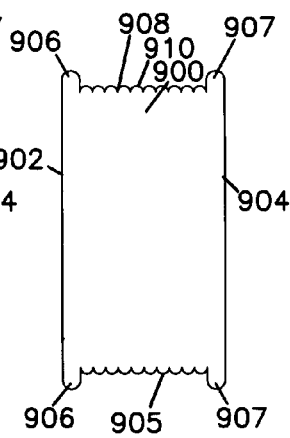
FIG. 27 is a side view of yet another alternative embodiment of a flossing aid adapted for use with the dental floss system of FIG. 1.
Figure 28:
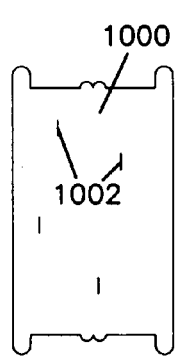
FIG. 28 is a side view of yet another alternative embodiment of a flossing aid adapted for use with the dental floss system of FIG. 1.

Ring 900 illustrated in FIG. 27 includes a first edge 902 and a second edge 904 and material 905 of varying thickness extending between the two edges. The material 905 defines a combination of a plurality of bumps 908 and grooves 910 along with flanges 906, 907 extending out radially at the first and second edges 902 and 904. As will be evident, any combination of flanges, sidewalls, grooves, and/or bumps within the spirit of the invention can be used according to desired functionality.

Figure 29:
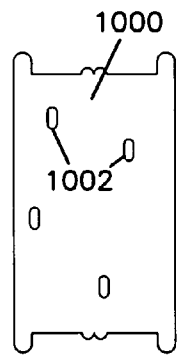
FIG. 29 is a side view of the flossing aid of FIG. 28, shown in a stretched position.
Figure 30:
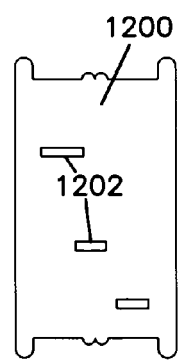
FIG. 30 is a side view of yet another alternative embodiment of a flossing aid adapted for use with the dental floss system of FIG. 1.
Figure 31:
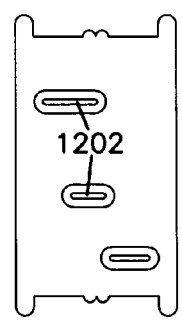
FIG. 31 is a side view of the flossing aid of FIG. 30, shown in a stretched position.

FIGS. 28-31 illustrate side views of two other embodiments of rings 1000 and 1200 wherein the rings include a plurality of slits 1002 and 1202 extending through the material. Slits 1002 and 1202 are adapted to allow the rings 1000 and 1200 to stretch more easily, providing more comfort to the finger when the finger is in a bent orientation. The ring 1000 includes slits 1002 extending perpendicular to the axial direction of the ring and the ring 1200 includes slits 1202 extending generally along the axial direction of the ring. FIGS. 29 and 31 illustrate how the slits 1002 and 1202 would appear upon stretching of the rings around the finger. The slits 1002 and 1202 shown in FIGS. 28-30 can certainly be used in combination with radially extending grooves, bumps, and/or flanges in various embodiments of the invention. The slits can be of different sizes and shapes and can be placed in various orientations around the perimeter of the material of the ring.

Although FIGS. 20-31 illustrate embodiments wherein the thickness variations of the material or density of the holes and slits are distributed in a symmetrical manner, in all the embodiments discussed, variations in the thickness of the material or the density of slits may be distributed in an asymmetrical manner. The density of the slits can vary depending on the desired functionality. For example, parts of the ring may have slits while other parts of the same continuous ring do not. The thicknesses of portions of the embodiments of the ring can vary non-uniformly depending on the desired functionality. For example, a ring may have uniform thickness throughout the material except for the area contacting the top portion of a finger, which is typically bonier. The top portion of the finger refers to the side of the finger opposite from the palm of the hand. This area may have thicker material than the rest of the ring. Other variations of the concept of non-uniform variable thickness and non-uniform density of holes or slits will be evident to one of ordinary skill in the art and come within the scope and spirit of the invention.

In another embodiment, the portion of the ring that will contact the top portion of the finger may have a portion that is stiffer than the remainder of the ring. The top portion of a finger may benefit from more protection from the floss. A stiffer portion at the top of the finger should be sized as not to cause discomfort to adjacent finger segments when the finger is flexed. The stiffness can be achieved by varying certain properties of the material such as durometer, the thickness of the material, the hardness of the material, etc.

Figure 32:
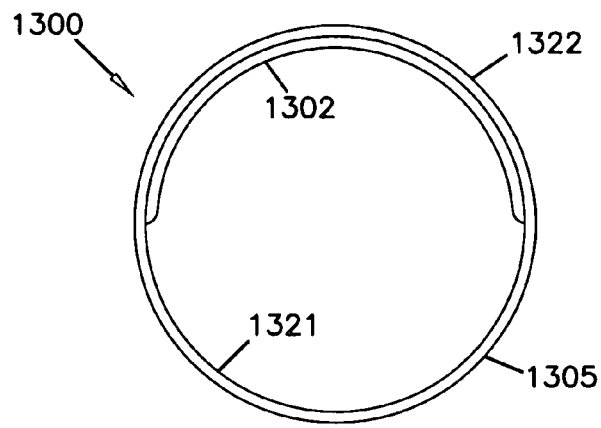
FIG. 32 is a top view of yet another alternative embodiment of a flossing aid adapted for use with the dental floss system of FIG. 1.

Also, as illustrated in the embodiment of the ring 1300 in FIG. 32, a rigid portion may be provided on the ring. In the embodiment of the ring 1300, the rigid portion is provided by having a liner 1302 added to the inner surface 1321 of the material 1305 of the ring 1300. The liner may be made from materials such as PVC, HDPP, HDPE, etc. The liner 1302, in addition to providing structural support and stability, may also provide a slicker inner surface as described previously making it easier to slide the ring 1300 onto the finger. It should also be understood that a liner is not necessary to provide the structural support for the flossing aid. A stiff material can also be integrally molded within the stretchable material of the flossing aid or be completely enveloped by the stretchable material as opposed to being formed on a surface of the ring. Different stiffnesses can be provided in different portions of the ring depending on the desired functionality.

In the embodiment illustrated in FIG. 32, the liner extends about halfway around the inner perimeter of the ring 1300, being located at the upper portion. Although the liner may be provided to extend around the entire inner perimeter of the ring, the embodiment shown in FIG. 32 may be preferable. The portion of the material 1305 below the liner 1302 allows the ring to be stretchable radially and allows the ring 1300 to fit multiple finger sizes. The portion of the material 1305 below the liner may also be deformable in the axial direction of the ring (as illustrated in FIG. 5B) to provide comfort when bending the finger. Since a liner such as the liner 1302 may be provided on the inner surface 1321 of the ring, the outer surface 1322 of the ring can still provide the softness and the frictional properties needed to grip the floss when the floss is wrapped around the flossing aid.

Figure 33:
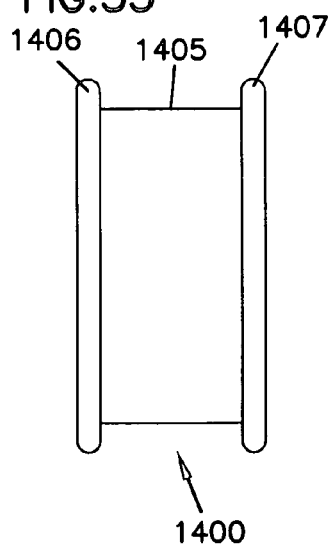
FIG. 33 is a side view of yet another alternative embodiment of a flossing aid adapted for use with the dental floss system of FIG. 1.

In another embodiment of the ring 1400 illustrated in FIG. 33, the ring may include flanges 1406 and 1407 (similar to the embodiments of FIGS. 24, 26, 27) made of stiffer material such as in the liner of FIG. 32. The stiffer flanges 1406 and 1407 would facilitate the sliding of the ring onto the finger while leaving a portion of soft material 1405 between the flanges to grip the floss and provide comfort to the user. The soft material 1405 would be deformable in the axial direction of the ring 1400 (as illustrated in FIG. 5B. The flanges 1406 and 1407, in addition to providing stiffness for ease of slidability, would also act as guides to assist the user in wrapping the floss on the ring 1400, as discussed previously for the embodiment of FIG. 24.

Figure 34:
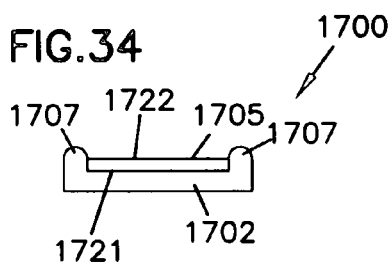
FIG. 34 is a partial cross-sectional view of yet another alternative embodiment of a flossing aid adapted for use with the dental floss system of FIG. 1, the cross section taken along a line similar to line 7-7 of FIG. 5A.

As shown in a partial cross-sectional view in FIG. 34, an embodiment having a combination of the aspects of the embodiments of FIGS. 32 and 33 can also be used. In the embodiment of the ring 1700 shown in FIG. 34, the ring includes a liner 1702 disposed at the inner surface 1721, the liner also including flanges 1707 that extend upwards past the edges of the stretchable material 1705 of the ring. In FIG. 34, a partial cross sectional view taken along a line similar to line 7-7 of FIG. 5A is shown to show the relative orientation of the liner and the stretchable and flexible material 1705. As discussed for the embodiments of FIGS. 32 and 33, the liner may extend partially around the inner perimeter of the ring 1700, being located at the upper portion, or extend around the entire inner perimeter of the ring. In an embodiment where the liner 1702 extends partially around the inner perimeter, the portion without the liner can be axially deformable as discussed for FIG. 32.

Figure 35A:
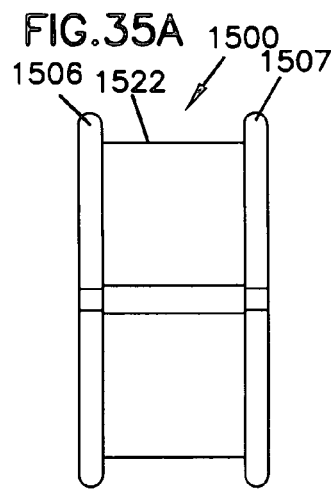
FIG. 35A is a side view of yet another alternative embodiment of a flossing aid adapted for use with the dental floss system of FIG. 1.
Figure 35B:
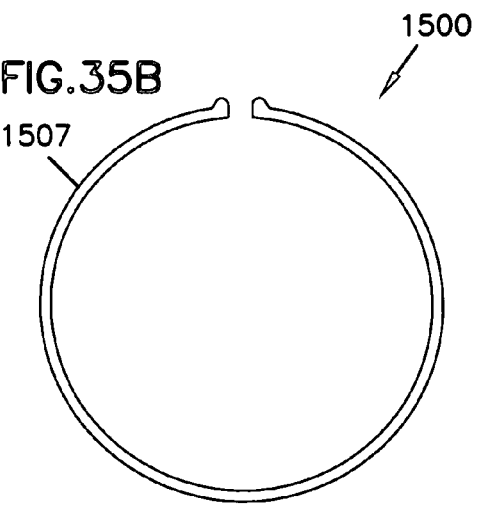
FIG. 35B is a top view of the flossing aid of FIG. 35A.
Figure 36:
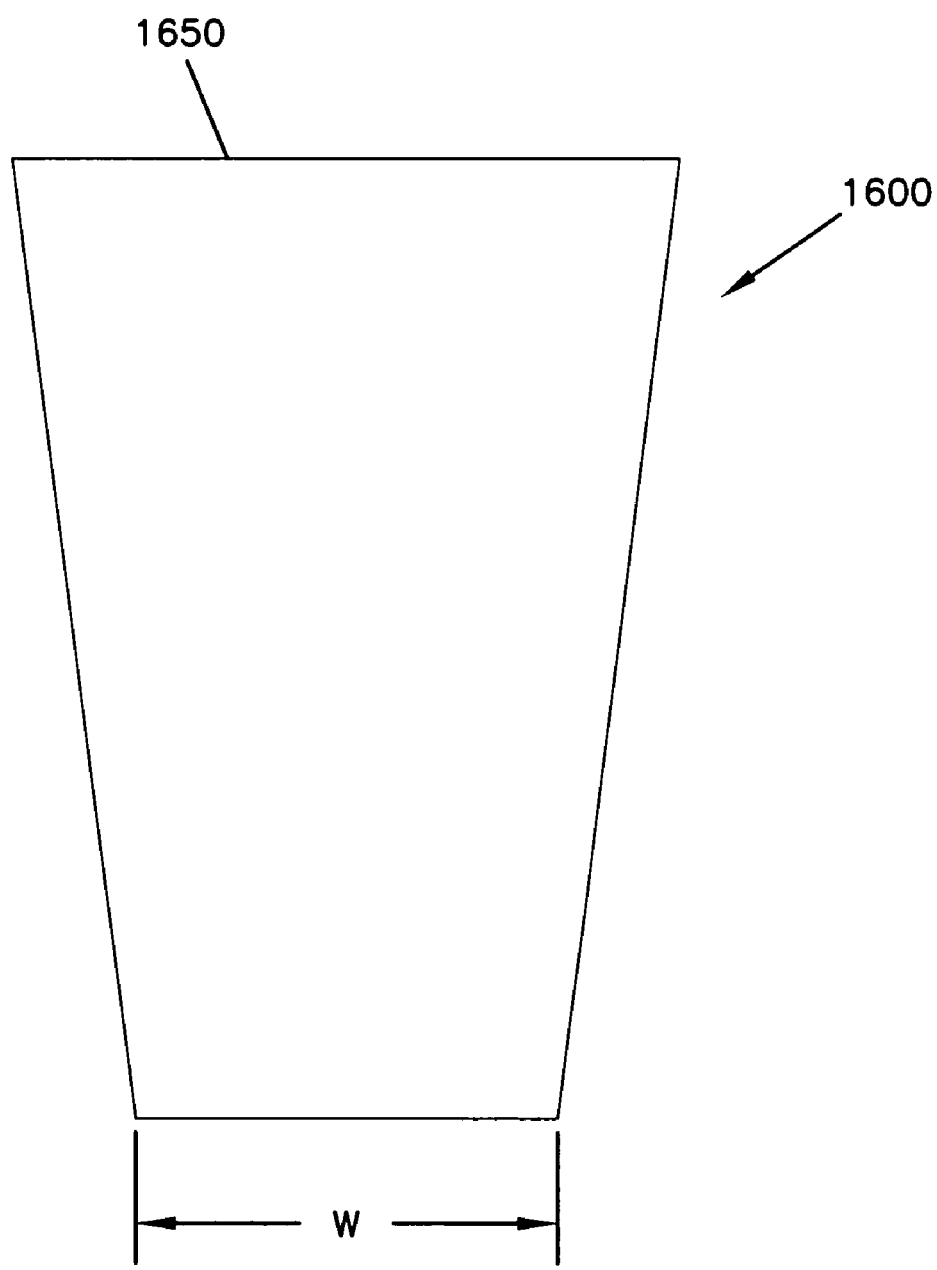
FIG. 36 is a side view of yet another alternative embodiment of a flossing aid adapted for use with the dental floss system of FIG. 1.

As mentioned previously, the flossing aid adapted to be used with the dental floss system of FIG. 1 may also include a split ring configuration. One example of a split ring design 1500 is illustrated in FIGS. 35A and 35B. FIG. 35A illustrates a side view of the split ring 1500 while FIG. 35B illustrates a top view. The split ring 1500 may be a variation of a design based on the embodiment in FIG. 33, wherein the ring includes flanges 1506 and 1507 that are made of a stiffer material wherein the material between the flanges may be softer to grip the floss. The ring 1500, however, also allows for radial flexibility due to its design to accommodate multiple sized finger such as the embodiment of FIG. 32. Although shown with flanges 1506 and 1507 that extend out radially from the outer surface 1522 of the ring 1500, in other embodiments, the split ring may certainly be provided without any flanges defined at the edges. Instead, the split ring may just have edges with stiffer portions to provide structural support for the split ring and to facilitate sliding onto the finger.

The inner finger-contacting surfaces of the embodiments of the rings of FIGS. 33 and 34 can also be provided with a slicker surface than the outer surfaces to facilitate sliding onto the finger, as mentioned above for previous embodiments.

Furthermore, although all the embodiments of the flossing aid have been described and shown as including a uniform width W (please refer to FIG. 3), it shall be understood that the flossing aids may include widths of varying dimension according to desired functionality, as mentioned previously. For example, as shown in FIG. 35, a ring 1600 may have a width W where the top portion 1650 of the ring 1600 is longer in an axial direction than the remainder of the ring.

D. Description of Flossing Methods Using the Invention

FIGS. 8-16 illustrate how the system including the ring 100 is used in combination with a length of floss 20 to floss teeth according to the invention. The method of flossing according to the invention will now be described by reference to the several drawing figures.

As illustrated in FIG. 1, the ring 100 is first placed on the middle finger 104, preferably on the middle segment or covering the outer-most knuckle. Alternatively, the ring may be placed on other fingers, either on a top or middle segment. The ring 100 is typically placed on at least the floss-receiving hand 106, which is normally the dominant hand. A second ring may also be placed on the floss-feeding hand. After the placement of the ring 100 around the middle finger 104 of the floss-receiving hand, a segment of a length of floss 20 is wrapped tightly around the outer surface 122 of the ring 100 at least once, preferably 1 to 3 times, overlapping itself at least once. As mentioned above, the wrapped segment 102 of the length of floss 20 will stay secure without another finger holding the floss in place because the material 101 of the ring 100 provides the necessary friction force. The friction between the outer surface 122 of the ring 100 and the wrapped segment 102 of floss increases as tension is increased on the length of floss 20. In addition to a greater downward force being created by the tension force, additional friction is provided by the fact that the wrapped segment 102 of floss digs into the material 101 of the ring 100. As previously mentioned, FIG. 7 illustrates how additional friction is created on the sides of the cross sectional perimeter of the ring 100. Also as seen in FIG. 5A, the ring 100 sinking into a soft part of the finger 104 provides an additional source of friction. Although the illustration shows ring 100 to be sinking into the finger 104, due to the flexibility of the material 101 of the ring 100, no discomfort will likely be experienced by the user.

After a segment of a length of floss is wrapped around the ring 100, the thumb and forefinger of the same hand 106 grasp the non-wrapped segment of the floss. Other fingers rest comfortably in a natural curled position.

Figure 8:
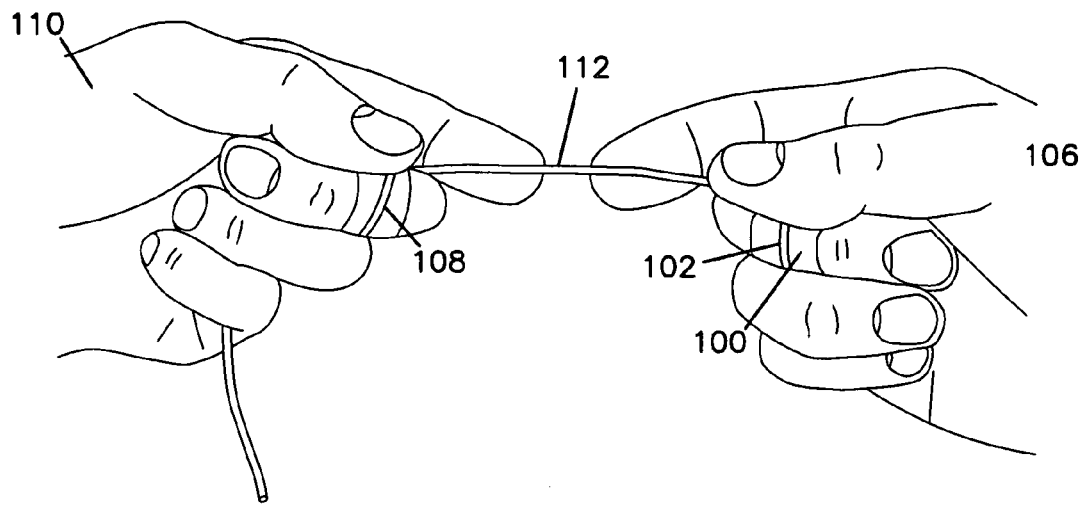
FIG. 8 is a perspective view of the dental floss system of FIG. 1, the hands are shown in a flossing position.

The other hand 110 is used to grab the non-wrapped, non-grasped end 108 of the floss. This hand 110 is the floss-feeding hand 110. Although FIG. 8 illustrates the floss-feeding hand 110 to have a ring 100 placed on the middle finger, it is not essential that a ring is worn on this hand. If a ring 100 however is used on the floss-feeding hand 110, the floss is normally wrapped around the ring 100 just as it is on the floss-receiving hand 106, except that it is normally wrapped to overlap itself only once on the outer surface of the ring 100. The grabbed segment 108 of the length of floss 20 can be wrapped additional times around the middle finger of the floss-feeding hand 110 depending on how slippery the floss is. The loose floss on the floss-feeding hand 110 can be hung down between the last two fingers, and the floss can be grasped lightly with the last two fingers for additional friction, as needed, as illustrated in FIG. 8. Bending the finger with the ring increases the friction as discussed above. The friction applied by the tension on the floss on both hands is sufficient to hold the floss in place without the thumbs holding the floss down. The thumbs on both hands can rest against the ring if this is comfortable for the user. A flossing segment 112 of the length of floss 20 between the two hands is used to floss the teeth.

As the teeth are flossed, the soiled floss can be repeatedly wrapped around the ring 100 of the middle finger 104 of the floss-receiving hand 106, so that new, non-soiled floss is available for the flossing segment 112 of the length of floss 20 between the two hands. Because of the ring 100 on the middle finger 104 of the floss-receiving hand 106, the pressure exerted by each additional wrapping of soiled floss is not transferred directly to the finger tissue. The material 101 of the ring 100 dissipates the pressure by flexing and stretching, thus reducing the discomfort felt on the finger with the ring 100.

Figure 9:
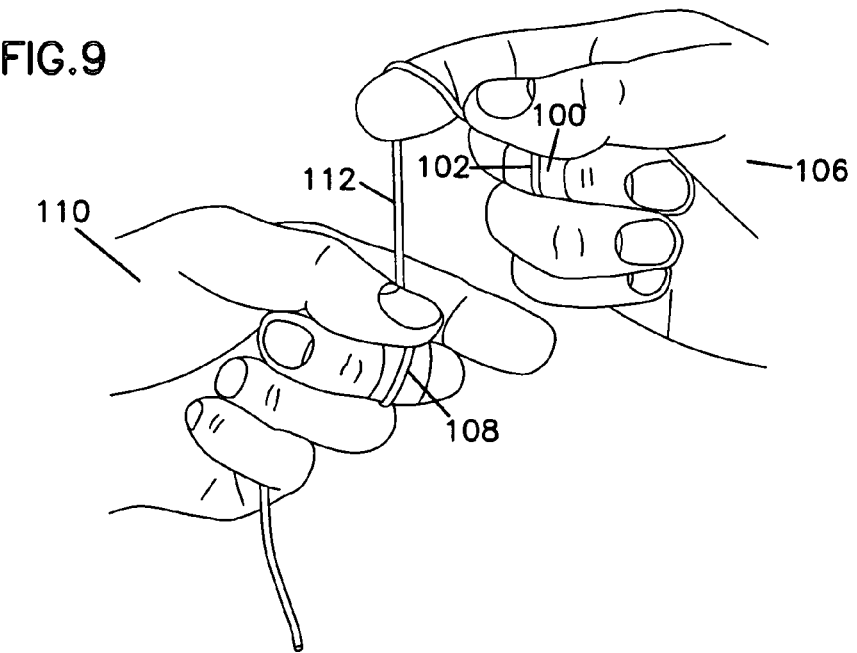
FIG. 9 is a perspective view of the dental floss system of FIG. 1, the hands are shown in a position after the floss has been partially unwound from the floss-receiving hand.

As the soiled floss is wrapped around the ring 100 of the floss receiving hand 106, more floss can be let out from the floss-feeding hand 110 to have non-soiled floss available on the flossing segment 112 of the length of floss 20. To let out more floss in the direction from the floss-feeding hand 110 to the floss receiving hand 106, the tension between the two hands is reduced. If the floss has been grasped on the loose hand with the last two fingers for additional support, the grip of the last two fingers of the floss-feeding hand 110 is relaxed also. If a ring is being worn on the floss-feeding hand 110 and if the finger wearing the ring has been bent, the finger is slightly straightened. The straightening of the ring-wearing finger normally reduces friction to a sufficient point to allow advancing of floss. If necessary, however, floss can be uncrossed from itself by rotating the floss-receiving hand 106 to partially unwind floss as illustrated in FIG. 9.

Figure 10:
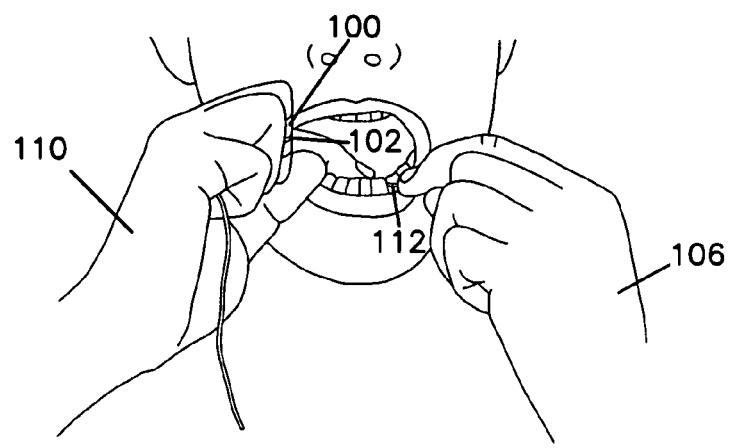
FIGS. 10-12 illustrate an embodiment of a method of flossing according to the invention pertaining to the bottom row of teeth.
Figure 11:
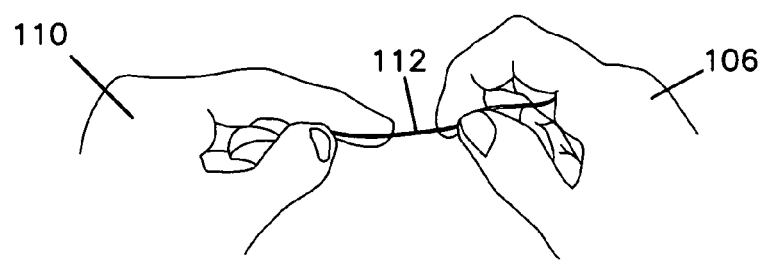
Figure 12:
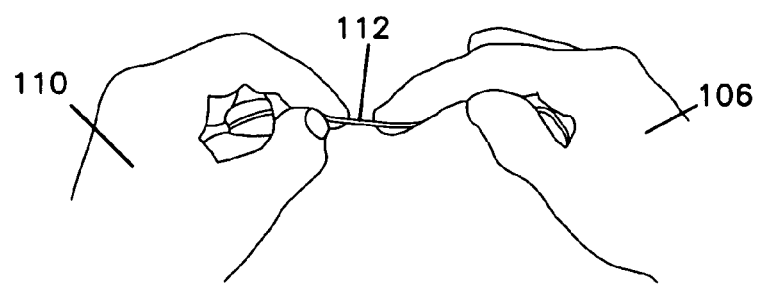

FIGS. 10-12 illustrate the method of flossing according to the invention as it pertains to the bottom row of teeth. It should be noted that the method of flossing teeth will be described from a perspective of a user whose dominant hand is his or her right hand and the dominant hand is used as the floss-receiving hand. It should be obvious to one in the art that the specific hands, specific fingers and other variables of the flossing techniques described herein may change depending on the different users.

As seen in FIG. 10, when flossing the bottom row of teeth, one segment of the floss is grabbed by the thumb and forefinger of the floss-receiving hand 106. Note that FIG. 10 illustrates an image that a user would see when looking into a mirror. In the floss-feeding hand 110, the index finger, staying straight, guides the flossing segment 112 into the mouth behind to the back teeth while the thumb stays outside the mouth. After entering the mouth, the user can guide the floss between teeth. The user can use gentle sawing action, being careful not to snap the floss between the teeth. Once between the teeth, the floss is curved around each tooth while the floss is moved up and down, going below the gum line.

If desired, non-soiled, fresh floss can be used for each tooth. Fresh floss can be used for several consecutive teeth without advancing more floss from the floss-feeding hand 110. Flossing several consecutive teeth without advancing more floss from the floss-feeding hand 110 can be done by flossing along the fixed flossing segment 112 between the two hands, starting near the floss-receiving hand 106, moving slightly toward the floss-feeding hand 110 after each tooth as illustrated in FIGS. 11 and 12. To facilitate flossing several consecutive bottom teeth without advancing more floss from the floss-feeding hand 110, a user can start with the floss-feeding hand 110 index finger extended and the floss-receiving hand 106 index finger/thumb bent as seen in FIG. 11. As the user proceeds from back teeth to the front, the floss-feeding hand 110 index finger/thumb can be slightly bent and the floss-receiving hand 106 index finger can be slightly straightened. FIG. 12 shows positioning of the hands after several bottom teeth have been flossed. New fresh floss is normally needed by the time the user gets to the middle teeth of the bottom row. The technique discussed for flossing several consecutive teeth without having to advance more floss from the floss-feeding hand 110 works well if the user starts flossing the bottom row of teeth in the back right area of the mouth. Typically, the back right area is the only section of the bottom row that the left index finger needs to be extended to reach.

Alternatively, instead of flossing several consecutive teeth without advancing more floss from the floss-feeding hand 110, fresh floss can be advanced for each tooth by releasing a small amount of floss in the direction from the floss-feeding hand 110 to the floss-receiving hand 106 after each tooth. With this technique, if needed, the soiled floss can be wrapped around the ring 100, as discussed earlier, after several teeth are flossed, or, if desired after each tooth is flossed. The technique is repeated for the other side of the bottom row reversing the orientation of the hands, however keeping the floss-feeding hand 110 and the floss-receiving hand 106 the same. The index finger of the hand inside the mouth is gradually straightened as the user moves to the back teeth of the bottom row. As needed, soiled floss can be wrapped around the ring 100 of the floss-receiving hand 106. New floss may then be advanced from the floss-feeding hand 110.

Figure 13:
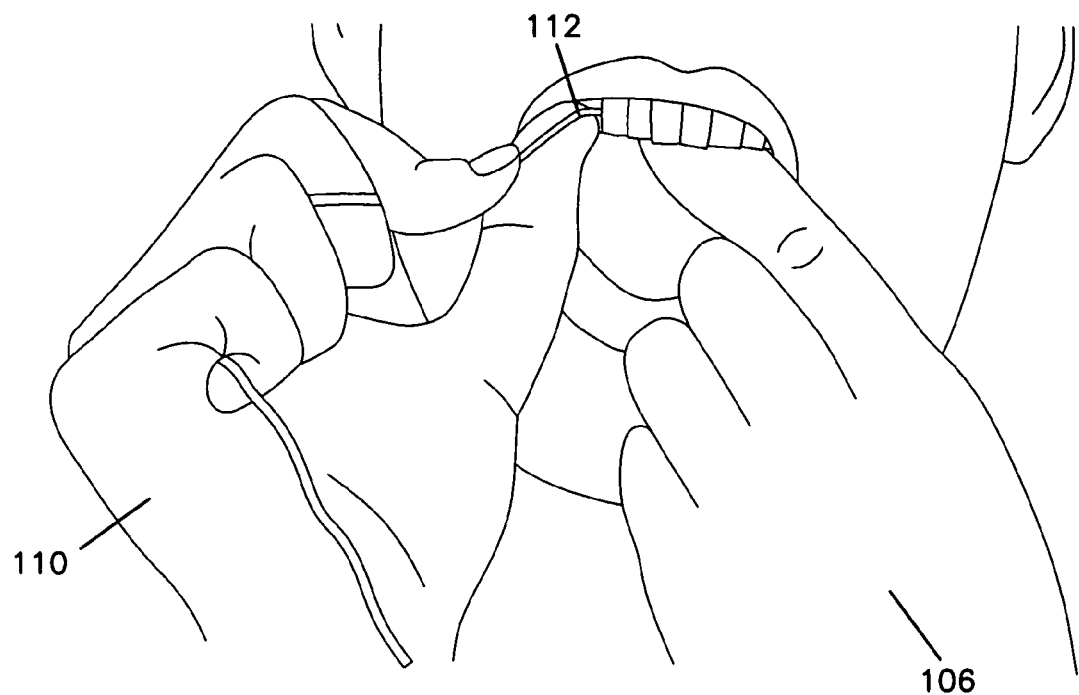
FIG. 13 illustrates an embodiment of a method of flossing according to the invention pertaining to the top row of teeth.

FIG. 13 illustrates the method of flossing according to the invention as it pertains to the top row of teeth. The thumb of the floss-feeding hand 110 remains outside the mouth as it guides the floss. The index finger of the floss-receiving hand 106 is straightened and guides the floss inside the mouth. As described for flossing the bottom row of teeth, floss is worked between each tooth, the user curving the floss around each tooth and moving it up and down, going below the gum line. Fresh floss is advanced as needed and soiled floss is taken up by the floss-receiving hand 106. This technique for the top row is repeated on both sides of the mouth, the thumb of the floss-feeding hand 110 staying outside the mouth and guiding the floss until the user reaches the middle teeth. Then the orientation of the hands is switched just as in the technique for the bottom row, however keeping the floss-feeding hand 110 and the floss-receiving hand 106 the same.

As described with respect to the bottom row, similar alternative techniques of advancing fresh floss and wrapping of soiled floss can be used for the top row of teeth.

As noted above, the method of flossing according to the invention was described from a perspective of a user whose dominant hand is the right hand, that hand also being the hand used to receive the soiled floss. The method was also described with the user wearing the flossing ring 100 only on the floss-receiving hand 106. It shall be appreciated that many modifications and variations can be made in the devices and the methods of the invention without departing from the spirit or scope of the invention. The following variations of the devices and the methods of the invention are for exemplary purposes and are not to be used to limit the scope of the invention.

Figure 14:
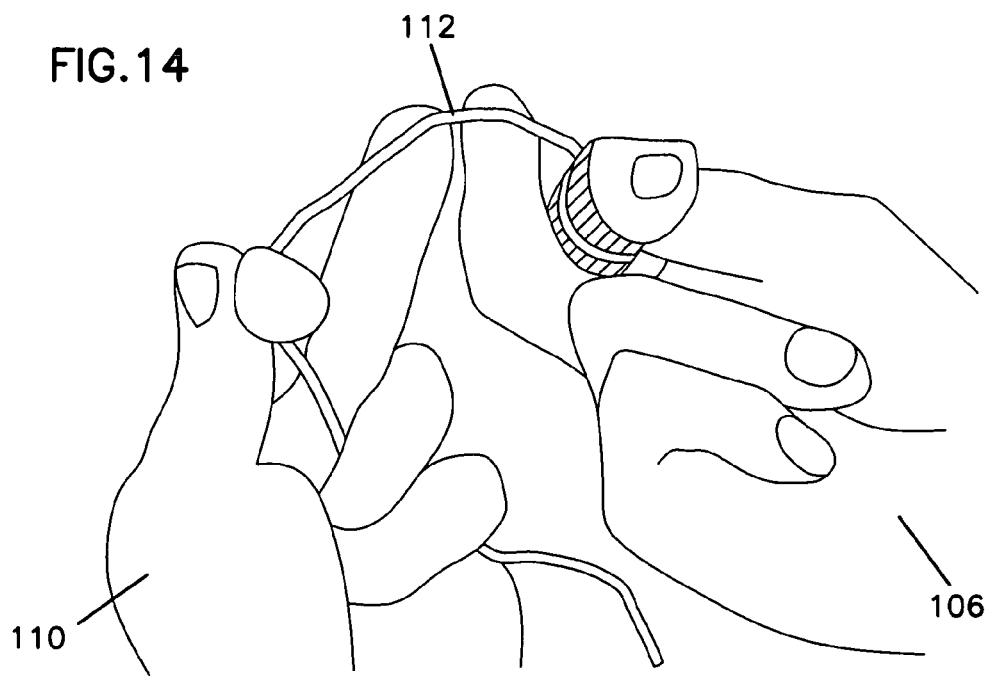
FIG. 14 illustrates an alternative embodiment of a method of flossing according to the invention pertaining to the top row of teeth.
Figure 15:
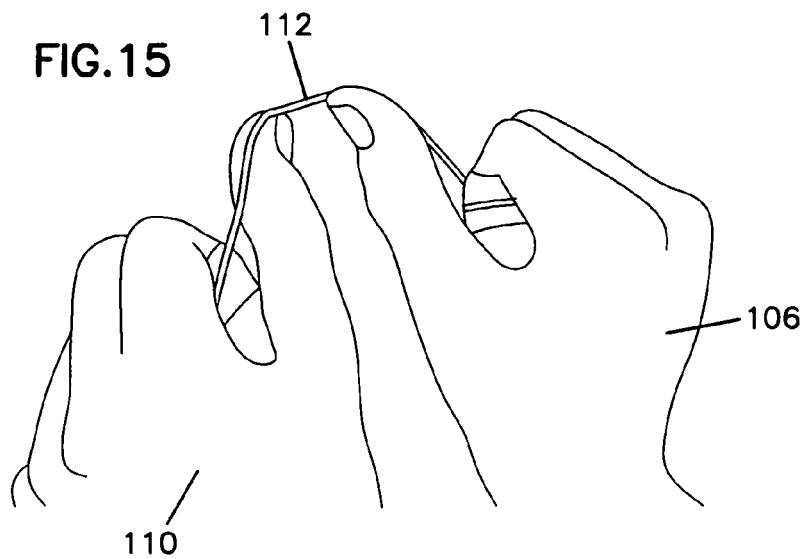
FIG. 15 illustrates yet another alternative embodiment of a method of flossing according to the invention pertaining to the top row of teeth.
Figure 16:
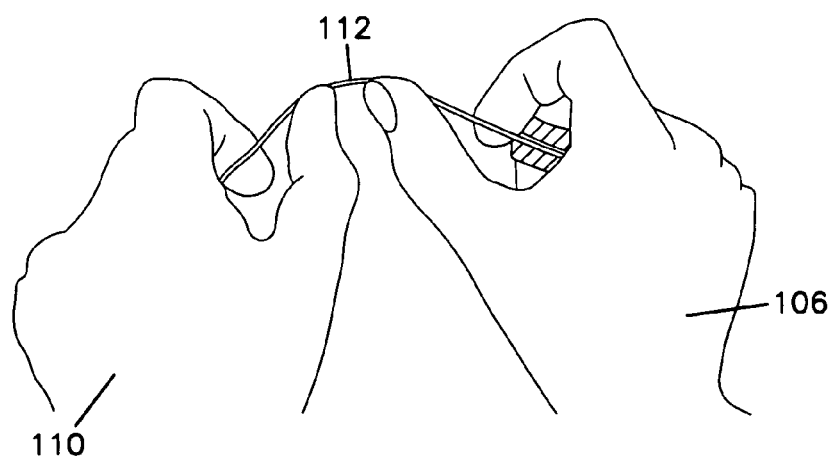
FIG. 16 illustrates yet another alternative embodiment of a method of flossing according to the invention pertaining to the top row of teeth.

In one possible alternative flossing technique, the user can wear the ring 100 on the fingertip of the finger instead of lower on the finger. The user can also reverse the order of flossing, starting on the top row of teeth instead of the bottom row, or the front instead of the back, or any combination thereof. The user can wear the flossing ring 100 around any finger on one or both hands or around any two or more fingers at the same time on one or both hands. The user can perform any of the above index-finger functions with the middle fingers for the bottom row of the teeth as illustrated in FIG. 14; the thumbs for the top row of teeth as illustrated in FIGS. 15 and 16; or the index finger on top row, bottom row, or both in any combination with the other fingers as discussed. The user may choose to wear the ring 100 around the index fingers while using the thumbs for index-finger functions for the top row of teeth as illustrated in FIG. 15. Alternatively, the user can wear the ring 100 around the middle fingers while using both the thumbs and the index fingers to guide the floss around the top row of teeth as illustrated in FIG. 16.

The user can choose whether or not to wear the flossing ring 100 on the floss-feeding hand 110. If the user decides to go without the ring 100 on the floss-feeding hand 110, the floss can be wrapped around any finger or a combination of fingers. The user can also weave the floss between any fingers for support. The user, if he or she chooses, can wear the flossing ring 100 on any one finger and wrap floss around more than one finger. The user can also wrap floss more than once around the ring 100 if worn on the floss-feeding hand 110.

The user may also choose not to use fresh floss for each tooth. The user may floss several teeth in a row using the same segment of floss, and if desired, periodically wrap soiled floss around the ring 100 and advance more floss from the floss-feeding hand 110.

The user may, when flossing the top row of teeth, on the outside hand, grasp floss with the index finger and thumb instead of guiding with the vertical thumb as was illustrated in FIG. 13.

The various embodiments described above are provided by way of illustration only and should not be construed to limit the invention. Those skilled in the art will readily recognize various modifications and changes which may be made to the present invention without strictly following the exemplary embodiments and applications illustrated and described herein, and without departing from the true spirit and scope of the present invention which is set forth in the following claims.

I claim:

1. A dental floss system comprising:
a) a length of dental floss; and
b) a flossing aid configured to be placed around a person's finger, the flossing aid configured to at least partially extend around the person's finger, the flossing aid defining a perimeter extending around the person's finger, the flossing aid including an inner surface configured to make contact with skin of the person's finger and an outer surface configured to make contact with a portion of the length of dental floss, the outer surface of the flossing aid that is configured to make contact with the dental floss including stretchable and flexible material, the flossing aid further including a liner formed of rigid material, the liner extending at least partially along the perimeter of the flossing aid, wherein the liner is located between the outer surface of the flossing aid and the skin of the person's finger.

2. A dental floss system according to claim 1, wherein the inner surface that is configured to make contact with the skin includes stretchable and flexible material.

3. A dental floss system according to claim 1, wherein the flossing aid includes a continuous ring.

4. A dental floss system according to claim 1, wherein the flossing aid includes a split ring.

5. A dental floss system according to claim 1, wherein the stretchable and flexible material includes natural or synthetic rubber.

6. A dental floss system according to claim 1, wherein the stretchable and flexible material has a durometer of about 25 to 50.

7. A dental floss system according to claim 1, wherein the stretchable and flexible material includes varying thickness along the perimeter.

8. A dental floss system according to claim 1, wherein the liner contacts the skin.

9. A dental floss system according to claim 1, wherein the liner is configured to not contact the skin.

10. A dental floss system comprising:
a) a length of dental floss; and
b) a flossing aid configured to be placed around a person's finger, the flossing aid defining a split-ring configuration with a first end and a second end and a gap located between the first end and the second end, the gap defining a split of the split-ring, the flossing aid defining a perimeter extending from the first end to the second end, the flossing aid configured to at least partially extend around the person's finger, the flossing aid including an inner surface configured to make contact with skin of the person's finger and an outer surface configured to make contact with a portion of the length of dental floss, the outer surface of the flossing aid that is configured to make contact with the dental floss including stretchable and flexible material, the flossing aid including a liner formed of rigid material, the liner extending at least partially along the perimeter of the flossing aid, wherein the liner is located between the outer surface of the flossing aid and the skin of the person's finger, the flossing aid further including a first protrusion extending from the outer surface, generally outwardly away from the person's finger when the flossing aid is placed around the person's finger, the first protrusion located adjacent the first end, the flossing aid including a second protrusion extending from the outer surface, generally outwardly away from the person's finger when the flossing aid is placed around the person's finger, the second protrusion located adjacent the second end, the first protrusion and the second protrusion configured to make contact with a portion of the length of dental floss.

11. A dental floss system according to claim 10, wherein the liner does not contact the skin.

12. A dental floss system according to claim 10, wherein the stretchable and flexible material includes natural or synthetic rubber.

13. A dental floss system according to claim 10, wherein the stretchable and flexible material has a durometer of about 25 to 50.

14. A dental floss system according to claim 10, wherein the stretchable and flexible material includes varying thickness along the perimeter.

15. A dental floss system according to claim 10, wherein the liner contacts the skin.

16. A dental floss system comprising:
a) a length of dental floss; and
b) a flossing aid configured to be placed around a person's finger, the flossing aid defining a split-ring configuration with a first end and a second end and a gap located between the first end and the second end, the gap defining a split of the split-ring, the flossing aid defining a perimeter extending from the first end to the second end, the flossing aid configured to at least partially extend around the person's finger, the flossing aid including an inner surface configured to make contact with skin of the person's finger and an outer surface configured to make contact with a portion of the length of dental floss, the outer surface of the flossing aid that is configured to make contact with the dental floss including stretchable and flexible material, the flossing aid including a liner formed of rigid material, the liner extending at least partially along the perimeter of the flossing aid, wherein the liner is located between the outer surface of the flossing aid and the skin of the person's finger.

17. A dental floss system according to claim 16, wherein the stretchable and flexible material includes natural or synthetic rubber.

18. A dental floss system according to claim 16, wherein the stretchable and flexible material has a durometer of about 25 to 50.

19. A dental floss system according to claim 16, wherein the stretchable and flexible material includes varying thickness along the perimeter.

20. A dental floss system according to claim 16, wherein the liner extends along the entire perimeter of the flossing aid.

* * * * *